United States Patent
Draheim et al.

(10) Patent No.: US 6,440,968 B1
(45) Date of Patent: Aug. 27, 2002

(54) USE OF MADURAOHTALAZINE DERIVATIVES AS INHIBITORS OF PROINFLAMMATORY CYTOKINES

(75) Inventors: Regina Draheim; Thomas Kronbach, both of Radebeul; Lothar Heinisch, Jena; Ernst Roemer, Bucha; Norbert Höfgen, Ottendorf-Okrilla; Hildegard Poppe, Dresden; Peter Jütten, Jena; Wolfgang Haas, Ichenhausen; Walter Werner; Udo Gräfe, both of Jena, all of (DE)

(73) Assignee: Elbion G.m.b.H., Redebenl (DE)

( * ) Notice: Subject to any disclaimer, the term of this patent is extended or adjusted under 35 U.S.C. 154(b) by 0 days.

(21) Appl. No.: 09/549,116

(22) Filed: Apr. 13, 2000

(30) Foreign Application Priority Data

Apr. 17, 1999 (DE) .......................................... 199 17 505

(51) Int. Cl.⁷ .................... A61K 31/502; C07D 237/32
(52) U.S. Cl. ........................................ 514/248; 544/233
(58) Field of Search ................................ 544/224, 233; 514/252, 248

(56) References Cited

FOREIGN PATENT DOCUMENTS

DE        WO/07706        *   7/1997

* cited by examiner

Primary Examiner—Richard L. Raymond

(57) ABSTRACT

The maduraphthalazine derivatives of the formula (4)

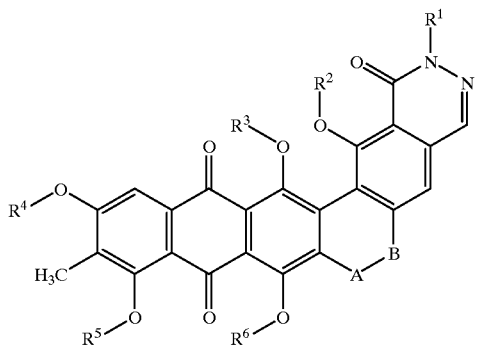

are able to inhibit the effect of the cytokines interleukin-2, interleukin-4 and interleukin-5 and are suitable for the production of pharmaceuticals.

7 Claims, No Drawings

USE OF MADURAOHTALAZINE DERIVATIVES AS INHIBITORS OF PROINFLAMMATORY CYTOKINES

FIELD OF THE INVENTION

The invention relates to the derivatives, both known and novel, of maduranic acid and their use as inhibitors of proinflammatory cytokines for producing pharmaceuticals for the treatment of disorders mediated by these cytokines, and process for making.

BACKGROUND

The immune system is a complicated network of interactions of different types of cells and their mediators with one another. The mediators are intercellular signal molecules which regulate, for example, the growth, the differentiation and the function of the cells involved (K. F. Arai et al., Annu. Rev. Biochem. 59 (1990), 783). One important group of mediators are the cytokines, which include the colony-stimulating factors and the interleukins. Cytokines are polypeptides whose diverse molecular characteristics, mechanisms of action, physiological functions and the part played by them in numerous disorders are currently the subjects of intensive research.

Thus, it is known that a number of cytokines are responsible for the control of the immunological defensive responses to pathogens. B lymphocytes and T lymphocytes are of crucial importance for identifying exogenous particles or substances and for initiating the cascade of defensive responses (H. Holtmann, K. Resch, Naturwissensch. 82 (1995), 178). The proliferation, the functional differentiation and the cell activity, but also the rate of release of other cytokines, are controlled for these cells in particular by interleukin-2 (IL-2) and interleukin-4 (IL-4) (W. J. Pichler, Schweiz. Med. Wochenschr. 127 (1997), 341). Both cytokines also act on the enhanced provision of interleukin-5 (IL-5). Thus, IL-2 is able to stimulate the synthesis of IL-5 in T lymphocytes (G. P. Anderson, A. J. Coyle, TiPS 15 (1994), 324).

IL-4 controls T-cell differentiation to increase production of Th2 cells which preferentially produce IL-4 and IL-5 (A. Mori et al., Intern. Immun. 8 (1996), 1889). The action of these 3 cytokines eventually initiates the pathogen-controlling responses which can be manifested as inflammation.

Numerous diseases are thought to be connected with disturbances of this system. Thus, excessive responses to non-hazardous foreign materials can be the cause of allergically induced disorders such as, for example, asthma, rhinitis, conjunctivitis or dermatitis. Immunological protective responses after transplants can lead to unwanted rejection reactions.

Substances able to inhibit the action of interleukin-2, interleukin-4 and interleukin-5 should thus be of great therapeutic benefit for treating disorders mediated by these cytokines.

Glucocorticosteroids such as, for example, beclomethasone or budesonide which have potent antuinflammatory and immunosuppressant activity have been demonstrated to inhibit IL-2,IL-4 and IL-5 (P. J. Barnes, Eur. Respir. J. 9 (1996) Suppl. 22, 154 and J. Schmidt et al., Europ. J. Pharm. 260 (1994), 247). Side effects such as an increase in intraocular pressure, increased susceptibility to infection, impairment of the hormonal control system (osteoporosis, growth retardation in children) can limit the use of glucocorticosteroids. Finally, cyclosporin A (CsA) has also been found to have an inhibitory effect on the three cytokines (B. Ryffel, Pharmacol. Rev. 41 (1989), 407). In this case various side effects have also been found (for example nephrotoxicity) (D. Faulds, K. L. Goa, P. Benfield, Drugs 45 (1993), 953).

The aim of this invention is to provide very active inhibitors of the cytokines interleukin-2, interleukin-4 and interleukin-5 and to produce pharmaceuticals for the treatment of disorders mediated by these cytokines.

Maduranic acid or madurahydroxylactone is a natural product obtained from *Actinomadura rubra* by fermentation (DD 285 614: W. F. Fleck, D. G. Strauss, J. Meyer, Z. Allg. Mikrobiol. 18 (1978) 368–398). The structure of this compound (Formula 1) was elucidated by Paulus and co-workers (E. F. Paulus, K. Dornberger, W. Werner, D. Fenske, Acta Cryst. C50 (1994) 2064–2067):

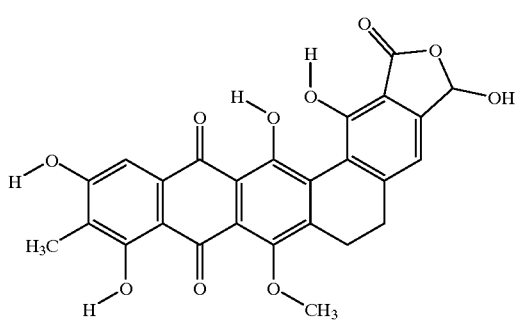

1

Antibacterial effects, preferentially on Gram-positive bacteria, have been described for this compound and its alkyl homologues (W. F. Fleck et al., Z. Allg. Mikrobiol. 18 (1978), 389).

In addition, the synthesis of some maduraphthalazine derivatives of Formula

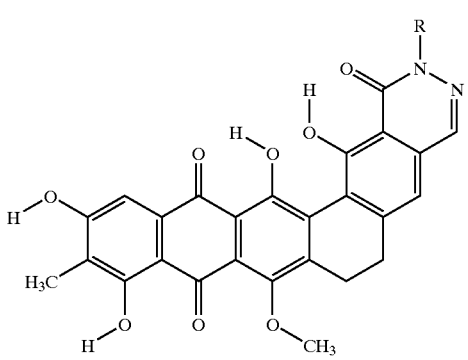

2 for example with —R: —H, —CH$_3$, —(CH$_2$)$_2$CH$_3$, —(CH$_2$)$_2$OH, -phenyl and of Formula 3

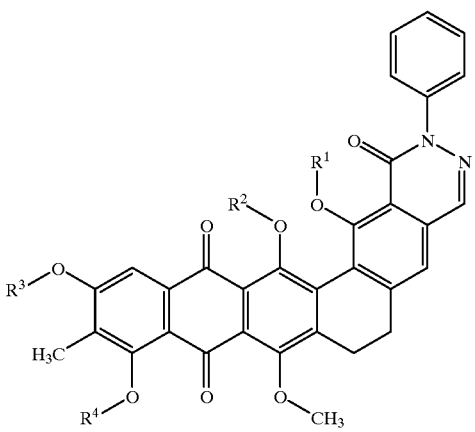

for example with

R¹=R²=R³=R⁴=—CH₃,
R¹=R²=R³=R⁴=—COCH₃,
R¹=R²=—H and R³=R⁴=—CH₃,
R¹=R²=—COCH₃ and R³=R⁴=—CH₃,
R¹=R²=R⁴=—H, and R³=—COCH₃ have been described, and their antimicrobial potential on some Gram-positive bacteria and bacterial gyrase have been investigated (E. Roemer et al., 4$^{th}$ Int. Conf. on Chemical Synthesis of Antibiotics and Related Microbial Products, Nashville, USA, 1994).

DESCRIPTION OF THE INVENTION

It has now been surprisingly found that both the previously known and many novel maduraphthalazines are able to inhibit the action of the cytokines interleukin-2, interleukin-4 and interleukin-5. Accordingly, these compounds are of great importance for producing pharmaceuticals for the therapy of disorders mediated by these cytokines. Thus, for example, it has been demonstrated that the compounds according to the present invention can inhibit the migration of eosinophilic granulocytes into the tissue which is characteristic of the asthmatic late phase reaction.

The invention thus relates to a process for inhibiting the action of the cytokines interleukin-2, interleukin4, and interleukin-5, which comprises administering to a patient in need therefore a compound of Formula 4

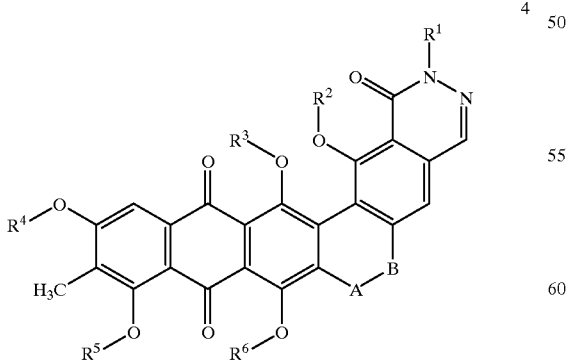

wherein

R¹ is hydrogen, or branched-chain, or straight-chain $C_{1-12}$alkyl residue optionally substituted one or m —$NHC_{6-14}$aryl, —$N(C_{6-14}aryl)_2$, —$N(C_{1-6}alkyl)$ ($C_{6-14}$aryl), —NHCOR⁷, —NO₂, —CN, —F, —Cl —Br, —I, —O—$C_{1-6}$alkyl, —O—$C_{6-14}$aryl, —O(CO) R⁷, —S—$C_{1-6}$-alkyl, —S—$C_{1-14}$aryl, —SOR⁸, —SO₂R⁸, —OSO₂$C_{1-6}$alkyl, —OSO₂$C_{6-14}$aryl, —(CS)R⁷, —O(CO)R⁷, —(CO)R⁹, a mono-, bi- or tricyclic saturated or mono- or polyunsaturated carbocycle with 3–14 ring members, mono-, bi- or tricyclic saturated or mono- or polyunsaturated heterocycle with 5–15 ring members and 1–6 heteroatoms, wherein the $C_{6-14}$aryl groups and the included carbocylic and heterocyclic substituents can be optionally substituted one or more times by R¹⁰, a mono- or polyunsaturated, straight-chain or branched-chain $C_{2-12}$alkenyl residue optionally substituted one or more times by —OH, —SH, —NH₂,—$NHC_{1-6}$alkyl, —$N(C_{1-6}alkyl)_2$, —$NHC_{6-14}$aryl, —$N(C_{6-14}aryl)_2$, —$N(C_{1-6}alkyl)$ ($C_{6-14}$aryl), —NHCOR⁷, —NO₂, —CN, —F, —Cl, —Br, —I, —O—$C_{1-6}$alkyl, —O—$C_{6-14}$-aryl, —O(CO)R⁷, —S—$C_{1-6}$alkyl, —S—$C_{6-14}$aryl, —SOR⁸, —SO₂R⁸, —OSO₂$C_{1-6}$alkyl, —OSO₂$C_{6-14}$aryl, —(CS)R⁷, —O(CO)R⁷, —(CO)R⁹, mono-, bi- or tricyclic saturated or mono- or polyunsaturated carbocycle with 3–14 ring members, a mono-, bi- or tricyclic saturated or mono- or polyunsaturated heterocycle with 5–15 ring members and 1–6 heteroatoms, the $C_{6-14}$ aryl groups and the included carbocyclic and heterocyclic substituents can be optionally substituted one or more times by R¹⁰, mono-, bi- or tricyclic saturated or mono- or polyunsaturated carbocycle with 3–14 ring members, optionally substituted one or more times by —OH, —SH, —NH₂,—NH $C_{1-6}$alkyl, —$N(C_{1-6}alkyl)_2$, —$NHC_{6-14}$aryl, —$N(C_{6-14}aryl)_2$, —$N(C_{1-6}alkyl)$ ($C_{6-14}$aryl), —NHCOR⁷, —NO₂, —CN, —F, —Cl, —Br, —I, —O—$C_{1-6}$-alkyl, —O—$C_{6-14}$aryl, —O(CO)R⁷, —S—$C_{1-6}$ alkyl, —S—$C_{6-14}$aryl, —SOR⁸, —SO₂R⁸, —OSO₂$C_{1-6}$alkyl, —OSO₂$C_{6-14}$aryl, —(CS)R⁷, —O(CO)R⁷, —(CO) R⁹, the $C_{6-14}$ aryl groups can be optionally substituted one or more times by R¹⁰, a mono-, bi- or tricyclic saturated or mono- or polyunsaturated heterocycle with 5–15 ring members and 1–6 heteroatoms, optionally substituted one or more times by —OH, —SH, —NH₂, —$NHC_{1-6}$alkyl, —$N(C_{1-6}alkyl)_2$, —$NHC_{6-14}$aryl, —$N(C_{6-14}aryl)_2$, —$N(C_{1-6}alkyl)(C_{6-14}aryl)$, —NHCOR⁷, —NO₂, —CN, —F, —Cl, —Br, —I, —O—$C_{1-6}$alkyl, —O—$C_{6-14}$aryl, —O(CO)R⁷, —S—$C_{1-6}$alkyl, —S—$C_{6-14}$aryl, —SOR⁸, —SO₂R⁸, —OSO₂$C_{1-6}$alkyl, —OSOC₂$C_{6-14}$aryl, —(CS)R⁷, —O(CO)R⁷, —(CO)R⁸, the $C_{6-14}$aryl groups can be optionally substituted one or more times by R¹⁰, carbo- or a heterocyclic saturated or mono- or polyunsaturated spirocycles with 3–10 ring members, where heterocyclic systems contain 1–6 heteroatoms optionally substituted one or more times by —OH, —SH, —NH₂, —$NHC_{1-6}$alkyl, —$N(C_{1-6}alkyl)_2$, —$NHC_{6-14}$aryl, —$N(C_{6-14}aryl)_2$, —$N(C_{1-6}alkyl)(C_{6-14}aryl)$, —NHCOR⁷, —NO₂, —CN, —F, —Cl, —Br, —I, —O—$C_{1-6}$ alkyl, —O—$C_{6-14}$aryl, —O(CO)R⁷, —S—$C_{1-6}$alkyl, —S—$C_{6-14}$aryl, —SOR⁸, —SO₂R⁸, —OSO₂$C_{1-6}$ alkyl, —OSO₂$C_{6-14}$ aryl, —(CS)R⁷, —O(CO)R⁷, —(CO)R⁸, the $C_{6-14}$aryl groups can be optionally substituted one or more times by R¹⁰;

$R^2$, $R^3$, $R^4$, $R^5$, $R^6$ can be the same or different and are hydrogen, and a straight-chain or branched-chain $C_{1-6}$alkyl residue, optionally substituted one or more times by —OH, —SH, —NH$_2$,—NHC$_{1-6}$alkyl, —N(C$_{1-6}$alkyl)$_2$, —NHC$_{6-14}$aryl, —N(C$_{6-14}$aryl)$_2$, —N(C$_{1-6}$alkyl)(C$_{6-14}$aryl), —NHCOR$^7$, —NO$_2$, —CN, —(CO)R$^8$, —(CS)R$^7$, —F, —Cl, —Br, —I, —O—C$_{1-6}$alkyl, —O—C$_{6-14}$aryl, —O(CO)R$^7$, —S—C$_{1-6}$alkyl, —S—C$_{1-14}$aryl, —SOR$^8$, —SO$_2$R$^8$, CO—C$_{1-6}$alkyl, optionally substituted one or more times by —OH, —SH, —NH$_2$, —NHC$_{1-6}$alkyl, —N(C$_{1-6}$alkyl)$_2$, —NHC$_{6-14}$aryl, —N(C$_{6-14}$aryl)$_2$, —N(C$_{1-6}$alkyl)(C$_{6-14}$aryl), —NHCOR$^7$, —NO$_2$, —CN, —(CO)R$^8$, —(CS)R$^7$, —F, —Cl, —Br, —I, —O—C$_{1-6}$alkyl, —O—C$_{6-14}$aryl, —O(CO)R$^7$, —S—C$_{1-6}$alkyl, —S—C$_{6-14}$aryl, —SO$^8$, —SO$_2$R$^8$ COO—C$_{1-6}$alkyl residue, optionally substituted one or more times by —OH, —SH, —NH$_2$, —NHC$_{1-6}$alkyl, —N(C$_{1-6}$alkyl)$_2$, —NHC$_{6-14}$aryl, —N(C$_{6-14}$aryl)$_2$, —N(C$_{1-6}$alkyl)(C$_{6-14}$aryl), —NHCOR$^7$, —NO$_2$, —CN, —(CO)R$^8$, —(CS)R$^7$, —F, —Cl, —Br, —I, —O—C$_{1-6}$alkyl, —O—C$_{6-14}$aryl, —O(CO)R$^7$, —S—C$_{1-6}$alkyl, —S—C$_{6-14}$aryl, —SOR$^8$, —SO$_2$R$^8$;

$R^7$ is a C$_{1-6}$alkyl, —O—C$_{1-6}$alkyl, —O—C$_{6-14}$aryl, —NH$_2$, —NHC$_{1-6}$alkyl, —N(C$_{1-6}$alkyl)$_2$, —NHC$_{6-14}$aryl, —N(C$_{6-14}$aryl)$_2$, —N(C$_{1-6}$alkyl)(C$_{6-14}$aryl), —S—C$_{1-6}$alkyl, —S—C$_{6-14}$aryl residue, or a mono-, bi- or tricyclic saturated or mono- or polyunsaturated carbocycle with 3–14 ring members, or mono-, bi- or tricyclic saturated or mono- or polyunsaturated heterocycle with 5–15 ring members and 1–6 heteroatoms, $R^8$ is —H, a —C$_{1-6}$alkyl, —NH$_2$,—NHC$_{1-6}$alkyl, —N(C$_{1-6}$alkyl)$_2$, —NHC$_{6-14}$aryl, —N(C$_{6-14}$aryl)$_2$, —N(C$_{1-6}$alkyl)(C$_{6-14}$aryl, —NHCOR$^7$, —OH, —O—C$_{1-6}$alkyl, —O—C$_{6-14}$aryl), —S—C$_{1-6}$alkyl, —S—C$_{6-14}$aryl residue, or a mono-, bi- or tricyclic saturated or mono- or polyunsaturated carbocycle with 3–14 ring members, or mono-, bi- or tricyclic saturated or mono- or polyunsaturated heterocycle with 5–15 ring members and 1–6 heteroatoms;

$R^9$ is —H, a —C$_{1-6}$alkyl residue, or mono-, bi- or tricyclic saturated or mono- or polyunsaturated carbocycle with 3–14 ring members, or a mono-, bi- or tricyclic saturated or mono- or polyunsaturated heterocycle with 5–15 ring members and 1–6 heteroatoms, $R^{10}$ is —OH, a —SH, —NH$_2$, —NHC$_{1-6}$alkyl, —N(C$_{1-6}$alkyl)$_2$, —NHC$_{6-14}$aryl, —N(C$_{6-14}$aryl)$_2$, —N(C$_{1-6}$alkyl)(C$_{6-14}$aryl), —NHCOR$^7$, —NO$_2$, —CN, —(CO)R$^8$, —(CS)R$^7$, —F, —Cl, —Br, —I, —O—C$_{1-6}$alkyl, —O—C$_{6-14}$aryl, —O(CO)R$^7$, —S—C$_{1-6}$alkyl, —S—C$_{6-14}$aryl, —SOR$^8$, or an —SO$_2$R$^8$ residue and A, B can be a —CH$_2$—, —CH(OH) residue or A+B can be a —CH=CH— residue, or with a pharmaceutically acceptable salt thereof The invention also relates to compounds and salts of Formula 4, wherein $R^1$ through $R^9$ have the same meanings as above, provided that $R^2$ through $R^5$ are not hydrogen when $R^6$ is CH$_3$.

The pharmacologically acceptable salts are obtained in a conventional manner by neutralizing the bases with inorganic or organic acids or by neutralizing the acids with inorganic or organic bases. Examples of suitable inorganic acids are hydrochloric acid, sulfuric acid, phosphoric acid or hydrobromic acid, and of organic acids are carboxylic or sulfonic acids such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, malic acid, salicylic acid, 3-aminosalicylic acid, ascorbic acid, embonic acid, nicotinic acid, isonicotinic acid, oxalic acid, amino acids, methanesulfonic acid, ethanesulfonic acid, 2-hydroxyethanesulfonic acid, ethane-1,2-disulfomic acid, benzenesulfonic acid, 4-methylbenzenesulfonic acid or naphthalene-2-sulfonic acid. Examples of suitable inorganic bases are sodium hydroxide solution, potassium hydroxide solution, ammonia, and of organic bases are amines, suitably tertiary amines such as trimethylamine, triethylamine, pyridine, N,N-dimethylaniline, quinoline, isoquinoline, -picoline, -picoline, -picoline, quinaldine or pyrimidine.

It is furthermore possible to obtain pharmacologically suitable salts of the compounds of Example 4 by converting derivatives which have tertiary amino groups into the corresponding quaternary ammonium salts with quaternizing agents in a manner known per se. Examples of suitable quaternizing agents are alkyl halides such as methyl iodide, ethyl bromide and n-propyl chloride, but also arylalkyl halides such as benzyl chloride or 2-phenylethyl bromide.

The invention further relates to the D form, the L form and D,L mixtures of compounds of Formula 4 which contain an asymmetric carbon atom and, in the case of a plurality of asymmetric carbon atoms, the diastereomeric forms. Compounds of Formula 4 which contain asymmetric carbon atoms and are usually obtained as racemates can be separated into the optically active isomers in a manner known per se, for example using an optically active acid. However, it is also possible to employ from the outset an optically active starting substance, in which case the final product obtained is a corresponding optically active or diastereomeric compound. p The invention relates to the use of the compounds of the present invention or their pharmacologically acceptable salts as inhibitors of the cytokines IL-2,IL-4 and IL-5 for producing pharmaceuticals for the treatment of disorders mediated by these cytokines.

These disorders include, for example, bronchial asthma, allergic rhinitis, allergic conjunctivitis, a topic dermatitis, eczemas, allergic angiitis, inflammations mediated by eosinophils, such as eosinophilic fasciitis, eosinophilic pneumonia and PIE syndrome, autoimmune diseases such as rheumatoid arthritis, rheumatoid spondylitis, lupus erythematosus, multiple sclerosis, psoriasis, glomerulonephritis and uveitis, insulin-dependent diabetes mellitus and sepsis.

The compounds according to the invention or their pharmacologically acceptable salts are also useful to produce pharmaceuticals for preventing rejection reactions after transplants of cells, tissues or organs. These pharmaceuticals are produced using an effective dose of the compounds according to the invention or their salts, in addition to conventional excipients, carriers and additives.

The dosage of the active ingredients can vary depending on the route of administration, age, weight of the patient, nature and severity of the disorders to be treated and similar factors. The daily dose can be given as a single dose to be administered once or divided into two or more doses a day, and is, generally between, 0.001 and 100 mg.

Oral, parenteral, intravenous, transdermal, topical, inhalation and intranasal preparations are suitable as administration forms.

Conventional pharmaceutical formulations are suitably used, such as tablets, coated tablets, capsules, dispersible powders, granules, aqueous solutions, aqueous or oily suspensions, syrups or drops.

Solid drug forms may contain inert ingredients and carriers such as, for example, calcium carbonate, calcium phosphate, sodium phosphate, lactose, starch, mannitol, alginates, gelatin, guar gum, magnesium or aluminium stearate, methylcellulose, talc, highly disperse silicas, silicone oil, higher molecular weight fatty acids (such as stearic acid), agar-agar or vegetable or animal fats and oils, solid high molecular weight polymers (such as polyethylene glycol); preparations suitable for oral administration may, if desired, contain additional flavorings and/or sweeteners.

Liquid drug forms may be sterilized and/or where appropriate contain excipients such as preservatives, stabilizers, wetting agents, penetrating agents, emulsifiers, spreading agents, solubilizers, salts, sugars or sugar alcohols to control the osmotic pressure or for buffering and/or viscosity regulators. Examples of additions of these types are tartrate and citrate buffers, ethanol, complexing agents (such as ethylenediaminetetraacetic acid and its non-toxic salts). Suitable for controlling the viscosity are high molecular weight polymers such as, for example, liquid polyethylene oxide, microcrystalline celluloses, carboxymethylcelluloses, polyvinylpyrrolidones, dextrans or gelatin. Examples of solid carriers are starch, lactose, mannitol, methylcellulose, talc, highly disperse silicas, higher molecular weight fatty acids (such as stearic acid), gelatin, agar-agar, calcium phosphate, magnesium stearate, animal and vegetable fats, solid high molecular polymers such as polyethylene glycol.

Oily suspensions for parenteral or topical uses may contain vegetable, synthetic or semisynthetic oils such as, for example, liquid $C_{8-22}$ fatty acid esters, for example palmitic, lauric, tridecylic, margaric, stearic, arachic, myristic, behenic, pentadecylic, linoleic, elaidic, brassidic, erucic or oleic acid, which are esterified with $C_{1-6}$ mono- to trihydric alcohols such as methanol, ethanol, propanol, butanol, pentanol or isomers thereof, glycol or glycerol. Examples of fatty acid esters of these types are commercially available Miglyols, isopropyl myristate, isopropyl palmitate, isopropyl stearate, PEG 6-capric acid, caprylic/capric esters of saturated fatty alcohols, polyoxyethylene glycerol trioleates, ethyl oleate, waxy fatty acid esters such as artificial duck preen gland fat, coconut fatty acid isopropyl ester, oleyl oleate, decyl oleate, ethyl lactate, dibutyl phthalate, diisopropyl adipate, polyol fatty acid esters inter alia. Likewise suitable are silicone oils varying in viscosity or fatty alcohols such as isotridecyl alcohol, 2-octyl dodecanol, cetyl stearyl alcohol or oleyl alcohol, fatty acids such as, for example, oleic acid. It is furthermore possible to use vegetable oils such as castor oil, almond oil, olive oil, sesame oil, cottonseed oil, peanut oil or soya oil.

Suitable solvents, gel formers and solubilizers are water or water-miscible solvents. Suitable examples are ethanol or isopropyl alcohol, benzyl alcohol, 2-octyldodecanol, polyethylene glycols, also phthalates, adipates, propylene glycol, glycerol, di- or tripropylene glycol, waxes, Methylcellosolve, Cellosolve, esters, morpholines, dioxane, dimethyl sulfoxide, dimethylformamide, tetrahydrofuran, cyclohexanone, etc.

Film formers which can be used are cellulose ethers which may dissolve or partly swell both in water and in organic solvents, such as, for example, hydroxypropylmethylcellulose, methylcellulose, ethylcellulose or soluble starches.

Mixed forms between gel formers and film formers are likewise possible. Used in this case are, in particular, ionic macromolecules such as, for example, sodium carboxymethylcelluose, polyacrylic acid, polymethacrylic acid and their salts, sodium amylopectin semiglycolate, alginic acid or propylene glycol alginate as sodium salt, gum arabic, xanthan gum, guar gum or carrageenan.

Further formulation aids which can be employed include glycerol, paraffin of varying viscosity, triethanolarmine, collagen, allantoin, novantisolic acid. It may also be necessary to use surfactants, emulsifiers or wetting agents for formulation, such as, for example, Na lauryl sulfate, fatty alcohol ether sulfates, di-Na N-lauryl-iminodipropionate, polyethoxylated castor oil or sorbitan monooleate, sorbitan monostearate, polysorbates (for example as sold under the name Tween), cetyl alcohol, lecithin, glycerol monostearate, polyoxyethylene stearate, alkylphenol polyglycol ethers, cetyltrimethylammonium chloride or mono/dialkyl polyglycol ether orthophosphoric acid monoethanolamine salts.

Stabilizers such as montmorillonite or colloidal silicas for stabilizing emulsions or for preventing the breakdown of the active substances such as antioxidants, for example tocopherols or butylated hydroxyanisole, or preservatives such as p-hydroxybenzoic esters, can likewise be used where appropriate for preparing the required formulations.

The products are manufactured and filled into containers and sealed under the usual antimicrobial conditions.

EXAMPLES

| Comp. | $R^1$ | $R^2$ | $R^3$ | $R^4$ | $R^5$ | $R^6$ | A | B |
|---|---|---|---|---|---|---|---|---|
| 1* | H | H | H | H | H | $CH_3$ | $CH_2$ | $CH_2$ |
| 2* | $CH_3$ | H | H | H | H | $CH_3$ | $CH_2$ | $CH_2$ |
| 3* | $(CH_2)_2CH_3$ | H | H | H | H | $CH_3$ | $CH_2$ | $CH_2$ |
| 4* | $(CH_2)_2OH$ | H | H | H | H | $CH_3$ | $CH_2$ | $CH_2$ |
| 5* | $C_6H_5$ | H | H | H | H | $CH_3$ | $CH_2$ | $CH_2$ |
| 6 | $(CH_2)_2OCOCH_3$ | H | H | H | H | $CH_3$ | $CH_2$ | $CH_2$ |
| 7* | $C_6H_5$ | H | H | $COOCH_3$ | H | $CH_3$ | $CH_2$ | $CH_2$ |
| 8 | $(CH_2)_2NH_2$ | H | H | H | H | $CH_3$ | $CH_2$ | $CH_2$ |
| 9 | 2-pyridyl- | H | H | H | H | H | $CH_2$ | $CH_2$ |
| 10 | $C_6H_5$ | H | H | H | H | H | $CH_2$ | $CH_2$ |
| 11 | $CH_2CH(OC_2H_5)_2$ | H | H | H | H | $CH_3$ | $CH_2$ | $CH_2$ |
| 12* | $C_6H_5$ | $COCH_3$ | $COCH_3$ | $COCH_3$ | $COCH_3$ | $CH_3$ | $CH_2$ | $CH_2$ |
| 13 | $C_6H_5$ | H | H | H | H | $CH_3$ | —CH= | =CH— |
| 14 | $C_6H_5$ | H | H | H | H | $CH_3$ | CHOH | CHOH |
| 15 | 2-imidazolyl- | H | H | H | H | $CH_3$ | $CH_2$ | $CH_2$ |

-continued

| Comp. | R¹ | R² | R³ | R⁴ | R⁵ | R⁶ | A | B |
|---|---|---|---|---|---|---|---|---|
| 16 | 2-pyridyl- | H | H | H | H | CH₃ | CH₂ | CH₂ |
| 17 | C₆H₅ | H | H | CH₂CH=CH₂ | H | CH₃ | CH₂ | CH₂ |

Compounds of the present invention can be prepared by synthesis methods per se, for example (with the parenthetical number following each compound name referring to the compound numbers in the foregoing table).

2-phenyl-10,12,15,16-tetrahydroxy-8-methoxy-11-methyl-9,14-dioxo-6,7,9, 14-tetrahydronaphthaceno[1,2-g]phthalazin-1-one (5)

A 5% mixture of madurahydroxylactone in glacial acetic acid is mixed with 2 mole equivalents of phenylhydrazine and boiled under reflux for 30 min. The reaction mixture is then left to stand at room temperature for about 12 hours. The red solid which has crystallized out is filtered off with suction, washed with glacial acetic acid and dried. The crude product is extracted with tetrahydrofuran (THF) in a Soxhlet. On cooling, the product crystallizes out and is filtered off with suction and dried. The yield is about 83% of theory.

mp: 350–353° C. (decomp.), MS ($C_{32}H_{22}N_2O_8$, M=562): m/z=563.0 [M+H]⁺.

The following compounds were prepared in an analogous manner:

10,12,15,16-Tetrahydroxy-8-methoxy-11-methyl-9,14-dioxo-6,7,9,14-tetrahydronaphthaceno[1,2-g]phthalazin-1-one (1)

mp: >360° C., MS ($C_{26}H_{18}N_2O_8$, M=486): m/z=487.2 [M+H]⁺.

2-Methyl-10,12,15,16-tetrahydroxy-8-methoxy-1-methyl-9, 14-dioxo-6,7,9,14-tetrahydronaphthaceno[1,2-g] phthalazin-1-one (2)

mp: >350° C., MS ($C_{27}H_{20}N_2O_8$, M=500): m/z =501.1 [M+H]⁺.

2-Propyl-10,12,15,16-tetrahydroxy-8-methoxy-11-methyl-9,14-dioxo-6,7,9,14-tetrahydronaphthaceno[1,2-g] phthalazin-1-one (3)

mp: 350–351° C., MS ($C_{29}H_{24}N_2O_8$, M=528): m/z=529.1 [M+H]⁺.

2-(2-Hydroxyethyl)-10,12,15,16-tetrahydroxy-8-methoxy-11-methyl-9,14-dioxo-6,7,9,14-tetrahydronaphthaceno[1,2-g]phthalazin-1-one (4)

mp: >300° C., MS ($C_{28}H_{22}N_2O_9$, M=530): m/z=531.1 [M+H]⁺.

2-(2-Acetoxyethyl)-10,12,15,16-tetrahydroxy-8-methoxy-11-methyl-9,14-dioxo-6,7,9,14-tetrahydronaphthaceno[1,2-g]phthalazin-1-one (6)

mp: >350° C., MS ($C_{30}H_{24}N_2O_{10}$, M=572): m/z=573.1 [M+H]⁺.

2-(2-Aminoethyl)-10,12,15,16-tetrahydroxy-8-methoxy-11-methyl-9,14-dioxo-6,7,9,14-tetrahydronaphthaceno[1,2-g]phthalazin-1-one (8)

mp: >350° C. (decomp.), MS ($C_{28}H_{25}N_3O_8$, M=529): m/z= 503.1 [M+H]⁺.

2-(2,2-Diethoxyethyl)-10,12,15,16-tetrahydroxy-8-methoxy-11-methyl-9,14-dioxo-6,7,9,14-tetrahydronaphthaceno[1,2-g]phthalazin-1-one (11)

mp: 285° C., MS ($C_{32}H_{31}N_2O_{10}$, M=603): m/z=604.1 [M+H]⁺.

2-(2-Imidazolyl)-10,12,15,16-tetrahydroxy-8-methoxy-11-methyl-9,14-dioxo-6,7,9,14-tetrahydronaphthaceno[1,2-g]phthalazin-1-one (15)

mp: >350° C. (decomp.), MS ($C_{29}H_{20}N_4O_8$, M=552): m/z= 553.1 [M+H]⁺.

2-(2-Pyridyl)-10,12,15,16-tetrahydroxy-8-methoxy-11-methyl-9,14-dioxo-6,7,9,14-tetrahydronaphthaceno[1,2-g]phthalazin-1-one (16)

mp: >350° C., MS ($C_{31}H_{21}N_3O_8$, M=563): m/z=564.1 [M+H]⁺.

The following further compounds were prepared using demethylmadurahydroxylactone as starting material in a manner analogously to Compound 5:

2-(2-Pyridyl)-8,10,12,15,16-pentahydroxy-11-methyl-9,14-dioxo-6,7,9,14-tetrahydronaphthaceno[1,2-g]phthalazin-1-one (9)

mp: >350° C., MS ($C_{30}H_{19}N_3O_8$, M=549): m/z=550.1 [M+H]⁺.

2-Phenyl-8,10,12,15,16-pentahydroxy-11-methyl-9,14-dioxo-6,7,9,14-tetrahydronaphthaceno[1,2-g]phthalazin-1-one (10)

mp: >350° C., MS ($C_{31}H_{20}N_2O_8$, M=548): m/z=549.1 [M+H]⁺.

Preparation of Demethylmadurahydroxylactone 40 m of a 35 per cent HBr in glacial acetic acid are added to a solution of 400 mg (0.8 mmol) of madurahydroxylactone in 50 m glacial acetic acid, and the mixture is heated to boiling for 1 hour. After cooling to room temperature, the reaction mixture is evaporated to dryness. The crude product is extracted with TBF. 280 mg of demethylmadurahydroxylactone are obtained. The yield is 75% of theory. mp: >350° C. (decomp.), MS ($C_{25}H_{16}O_{10}$, M=476): m/z=477.3 [M+H]⁺.

2-Phenyl-10,15,16-trihydroxy-8-methoxy-12-methoxycarbonyloxy-11-methyl-9,14-dioxo-6,7,9,14-tetrahydronaphthaceno[1,2-g]phthalazin-1-one (7)

A solution of 281.2 mg (0.5 mmol) of 2-phenyl-10,12, 15,16-tetrahydroxy-8-methoxy-11-methyl-9,14-dioxo-6,7,9,14-tetrahydronaphthaceno[1,2-g]phthalazin-1-one (5) in 2 m of 2 M sodium hydroxide solution is diluted with 5 m of water. This solution is equilibrated at 5° C. and, while stirring, 2 m of methyl chloroformate are added. The mixture is subsequently stirred at room temperature for 30 min and then neutralized with acetic acid. The precipitated product is filtered off with suction to obtain 260 mg of the product. The yield is 84% of theory.

mp: >350° C., MS ($C_{34}H_{24}N_2O_{10}$, M=620): m/z=621.0 [M+H]⁺.

2-Phenyl-10,12,15,16-tetraacetoxy-8-methoxy-11-methyl-9,14-dioxo-6,7,9,14-tetrahydronaphthaceno[1,2-g] phthalazin-1-one (12)

0.5 m each of acetic anhydride and pyridine are added to a solution of 167 mg (0.3 mmol) of 2-phenyl-10,12,15,16-tetrahydroxy-8-methoxy-11-methyl-9,14-dioxo-6,7,9,14-tetrahydronaphthaceno[1,2-g]phthalazin-1-one (5) in 5 m of $CH_2Cl_2$. After addition of 1 mg of DMAP, the mixture is stirred at room temperature for 1 hour. For workup, the reaction mixture is acidified with dilute hydrochloric acid, and the aqueous phase is extracted with $CH_2Cl_2$. The combined organic phases are dried over $MgSO_4$ and evaporated to dryness. 180 mg of the product are obtained. The yield is 83% of theory.

mp: 273° C., MS ($C_{40}H_{30}H_2O_{12}$, M=730.7): m/z=731.5 [M+H]$^+$.

2-Phenyl-12-allyl-10,15,16-trihydroxy-8-methoxy-11-methyl-9,14-dioxo-6,7,9,14-tetrahydronaphthaceno[1,2-g]phthalazin-1-one (17)

To a solution of 1 g (1.78 mmol) of 2-phenyl-10,12,15,16-tetrahydroxy-8-methoxy-11-methyl-9,14-dioxo-6,7,9,14-tetrahydronaphthaceno[1,2-g]phthalazin-1-one (5) in 10 m of $CH_2Cl_2$ are successively added, while stirring, at intervals of a few minutes 10 m of water, 10 mg of tetrabutylammonium bromide, 120 mg (3 mmol) of finely powdered sodium hydroxide and 0.26 m (2.8 mnmol) of allyl bromide. After 24 h at room temperature, the mixture is diluted with 40 m of water and acidifed with 10 per cent aqueous HCl. The organic phase is separated off, and the aqueous phase is extracted twice with 30 m of $CH_2Cl_2$. The combined organic phases are dried over $MgSO_4$ and, without previous concentration, filtered through 20 g of silica gel 60, eluted with $CH_2Cl_2$ until colourless, and evaporated to dryness. 370 mg of the product are obtained. The yield is 35% of theory.

mp: 163° C., MS ($C_{35}H_{26}N_2O_8$, M=602): m/z=603.0 [M+H]$^+$.

2-Phenyl-10,12,15,16-tetrahydroxy-8-methoxy-11-methyl-9,14-dioxo-9,14-dihydronaphthaceno[1,2-g]phthalazin-1-one (13)

A spatula tip of dibenzoyl peroxide is added to a mixture of 1.1 g (1.5 mmol) of 2-phenyl-10,12,15,16-tetraacetoxy-8-methoxy-11-methyl-9,14-dioxo-6,7,9,14-tetrahydronaphthaceno[1,2-g]phthalazin-1-one (12) and 0.53 g (3 mmol) of N-bromosuccinimide in 120 m of tetrachloromethane and 30 m of 1,1,2,2-tetrachloroethane, and the mixture is stirred under gentle reflux until conversion is complete. After cooling, the reaction mixture is washed with $Na_2S_2O_3$ solution and water. The solution dried over $Na_2SO_4$ is evaporated to dryness. The residue is dissolved in 20 m of tetrahydrofuran and, while cooling in ice, 2.1 m of sym-collidine are added. The reaction mixture is stirred overnight and then poured into an ice-cold dilute citric acid solution. The product is extracted with dichloromethane, and the combined organic phases are dried over $Na_2SO_4$ and concentrated.

A solution of 112 mg (0.15 mmol) of the resulting intermediate 2-phenyl-10,12,15,16-tetraacetoxy-8-methoxy-11-methyl-9,14-dioxo-9,14-dihydronaphthaceno[1,2-g]phthalazin-1-one in 2.3 m of N,N-dimethylformamide is mixed, while cooling in ice, with 2.3 m of 1 M potassium hydroxide solution and stirred at room temperature for 2 hours. The product is precipitated as a red solid (78 mg) by acidification with aqueous citric acid. The yield is 93% of theory.

MS ($C_{23}H_{20}N_2O_8$, M=560): m/z=561 [M+H]$^+$.

2-Phenyl-6,7,10,12,15,16-hexahydroxy-8-methoxy-11-methyl-9,14-dioxo-6,7,9,14-tetrahydronaphthaceno[1,2-g]phthalazin-1-one (14)

222 mg (0.88 mmol) of osmium(VIII) tetroxide and 142 μl (1.77 mmol) of pyridine are added to a solution of 516 mg (0.71 mmol) of 2-phenyl-10,12,15,16-tetraacetoxy-8-methoxy-11-methyl-9,14-dioxo-9,14-dihydronaphthaceno [1,2-g]phthalazin-1-one in 7 m of dioxane. The mixture is then stirred at room temperature for 6 days. To decompose the osmic ester, the mixture is diluted with ethanol and, after addition of an aqueous solution of $NaHSO_3$, stirred vigorously for 1 h. The product is extracted with $CH_2Cl_2$, and the combined organic phases are washed with water and dried over $Na_2SO_4$. The crude product is absorbed onto silica gel and eluted with 5:1 toluene/methanol. 371 mg of a dark yellow solid are obtained.

A solution of 100 mg (0.13 mmol) of the resulting intermediate 2-phenyl-10,12,15,16-tetraacetoxy-6,7-dihydroxy-8-methoxy-11-methyl-9,14-dioxo-9,14-dihydronaphthaceno[1,2-g]phthalazin-1-one in 2 m of N,N-dimethylformamide is mixed, while cooling in ice, with 2 m of 1 M potassium hydroxide solution and stirred at room temperature for 2 h. The product is precipitated as a red solid (60 mg) by acidification with aqueous citric acid. The yield is 77% of theory.

MS ($C_{32}H_{22}N_2O_{10}$, M=594): m/z=595 [M+H]$^+$.

To determine the effect of the compounds according to the invention on the said cytokines, the inhibition of the release of IL-2, IL-4 and IL-5 from T cells was investigated in vitro.

Inhibition of IL-2 Release from Jurkat Cells

Method:

Jurkat cells (clone E6-1, batch F-12871, from ATCC, Rockville, Md.) are seeded at about 100,000 cells in 50μ per well in microtitre plates and preincubated in an incubator (5% $CO_2$/37° C./100% humidity). The medium employed is RPMI-1640 with HEPES/10% FCS/2 mM glutamine/100 U/m penicillin/100 mg/m streptomycin and 50 μM mercaptoethanol. After 3 hours, the substances to be tested are applied in various concentrations (100μ per well). To determine the spontaneous value and maximum values, in each case only medium/0.2% DMSO is applied. 30 minutes after application of substance and incubation, stimulation is carried out with in each case 25μ of ionomycin (final concentration 1 μM, Sigma I-0634) and phorbol myristate acetate (PMA, final concentration 25 ng/m, Sigma P-8139) per well. The spontaneous value receives 50μ of medium in place of ionomycin/PMA. Incubation overnight is then carried out. The supernatants are measured undiluted in an IL-2 ELISA (Pharmingen, capture mab: 18951 D detection mab: 20672 D). The $IC_{50}$ determination was analysed by a logit-log plot.

| Compound | $IC_{50}$ [μmol/l] |
|---|---|
| 1 | 0.08 |
| 5 | 0.20 |

Inhibition of IL-4 Release from D10.G4.1 Cells (D10)

Method:

3 days after thawing and cultivating D10 cells in medium (RPMI-1640 with HEPES/10% FCS/2 mM glutamine/100 U/m penicillin/100 mg/m streptomycin and 50 μM mercaptoethanol) with Rat Stim™ (Collaborative Biomedical Products, Bedford Mass.) they are spun down, washed with medium without Rat Stim™, seeded at a concentration of 40,000 to 60,000 cells per well in a microtitre plate and incubated at 37° C./5% $CO_2$/100% humidity for 3.5 hours. The substances to be tested are then applied in various concentrations in each case 50μ per well. The determinations of the maximum value and spontaneous value each receive 50μ of medium/0.4% DMSO.

After a further 30 minutes of incubation, stimulation is carried out with in each case 50μ of anti-CD3 antibody (145-2C11, Cedarlane Laboratories Limited, Hornby/Ontario) per well (final dilution 1:100). The determination of the spontaneous value receives 50μ of medium. After incubation overnight, the supernatants are measured in an IL-4 ELISA (Pharmingen: capture mab: 18031D; detection mab: 18042 D). The $IC_{50}$ determination was analysed by a logit-log plot.

| Compound | IC$_{50}$ [μmol/l] |
|---|---|
| 1 | 0.86 |
| 2 | 1.46 |
| 3 | 2.91 |
| 8 | 2.58 |

Inhibition of IL-5 Release from D10.G4.1 Cells
(D10)

Method:

3 days after thawing and cultivating D10 cells in medium (RPMI-1640 with HEPES/10% FCS/2 mM glutamine/100 U/m penicillin/100 mg/m streptomycin and 50 μM mercaptoethanol) with Rat Stirm™ (Collaborative Biomedical Products, Bedford Mass.) they are spun down, washed with medium without Rat Stim™, seeded at a concentration of 40,000 to 60,000 cells per well in a microtitre plate and incubated at 37° C./5% CO$_2$/100% humidity for 3.5 hours. The substances to be tested are then applied in various concentrations in each case 50μ per well. The determinations of the maximum value and spontaneous value each receive 50μ d of medium/0.4% DMSO. After a further 30 minutes of incubation, stimulation is carried out with in each case 50μ of anti-CD3 antibody (145-2C11, Cedarlane Laboratories Limited, Hornby/Ontario) per well (final dilution 1:100). The determination of the spontaneous value receives 50μ of medium. After incubation overnight, the supernatants are measured in an IL-5 ELISA (Pharmingen: capture mab: 18051D; detection mab: 18062 D). The IC$_{50}$ determination was analysed by a logit-log plot.

| Compound | IC$_{50}$ [μmol/l] |
|---|---|
| 1 | 0.45 |
| 2 | 0.88 |
| 5 | 0.43 |
| 8 | 0.78 |
| 16 | 0.52 |

The significance of the inhibition found for the cytokines IL-2, IL4 and IL-5 can be demonstrated in vivo for example by investigating the effect of the compounds according to the invention on the asthmatic late phase reaction.

Inhibition of the Late Phase Eosinophilia 24 h
After Challenge of Actively Sensitized Guinea Pigs
by Ovalbumin Inhalation Method:

The inhibition of the pulmonary infiltration of eosinophils by the substances is examined in an in vivo test on Dunkin-Hartley guinea pigs which have been actively sensitized against ovalbumin. The sensitization is effected by two subcutaneous injections of a suspension of 10 μg of ovalbumin together with 1 mg of aluminium hydroxide in 0.5 m of physiological saline as adjuvant at an interval of 14 days. 7 days after the second injection, the animals in the control group which have to be exposed to an ovalbumin aerosol are pretreated with mepyramine maleate (10 mg/kg i.p.) in order to protect from anaphylactic death. After 30 minutes, the animals are exposed in a plastic box for 30 sec to an ovalbumin aerosol (0.5 mg/m ) which is produced by an atomizer driven by compressed air (19.6 kPa). Control animals are exposed to an aerosol of physiological saline. 24 hours after the exposure to ovalbumin aerosol (challenge) the animals are anaesthetized with an overdose of ethylurethane (1.5 g/kg of body weight i.p.), and a bronchoalveolar lavage is carried out with 2×5 m of physiological saline. The lavage fluid is collected and centrifuged at 300 rpm for 10 min, and then the cell pellet is resuspended in 1 m of physiological saline. The eosinophils are stained using the Becton-Dickinson test kit (N.5877) for eosinophils and are counted in a Neubauer chamber. Each test includes 2 control groups (exposure to a physiological saline aerosol and exposure to an ovalbumin solution aerosol).

The test substances are administered intraperitoneally or orally as suspension in 10% polyethylene glycol 300 and 0.5% strength 5-hydroxyethylcellulose 2 hours before the allergen challenge. The control groups are treated with the vehicle in a form corresponding to the administration of the test substance. The number of animals in each control and test group is 3–10. The results are listed in the following table: Table:

| Com-pound | Dose [mg/kg] | Adminis-tration | Eosinophils 10$^6$/animal ± s | | | Inhibition |
|---|---|---|---|---|---|---|
| | | | A | B | C | |
| 1 | 10 | i.p.-2h | 1.9 ±0.75 | 0.51 ±0.20 | 0.38 ±0.12 | 112.4 |
| 5 | 10 | i.p.-2h | 1.9 ±0.75 | 0.85 ±0.12 | 0.38 ±0.12 | 85.0 |

A = eosinophils in the control group with ovalbumin challenge and vehicle
B = eosinophils in the substance-treated group with ovalbumin challenge
C = eosinophils in the control group with 0.9% strength NaCl challenge and vehicle
= mean deviation
s = standard deviation The compounds according to the invention are thus particularly suitable for producing pharmaceuticals for the treatment of disorders which are connected with the effect of eosinophils.

What is claimed is:

1. Compounds and salts of Formula 4

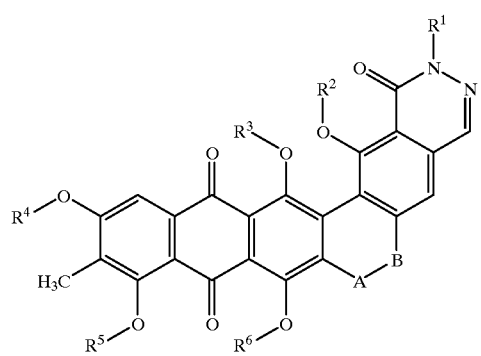

wherein

R$^1$ is hydrogen, or branched-chain, or straight-chain C$_{1-12}$alkyl residue optionally substituted one or more times by —OH, —SH, —NH$_2$, —NHC$_{1-6}$alkyl, —N(C$_{1-6}$alkyl)$_2$, —NHC$_{6-14}$aryl, —N(C$_{6-14}$aryl)$_2$, —N(C$_{1-6}$alkyl)(C$_{6-14}$aryl), —NHCOR$^7$, —NO$_2$, —CN, —F, —Cl, —Br, —I, —O—C$_{1-6}$alkyl, —O—C$_{6-14}$aryl, —O(CO)R$^7$, —S—C$_{1-6}$-alkyl, —S—C$_{6-14}$aryl, —SOR$^8$, —SO$_2$R$^8$, —OSO$_2$C$_{1-6}$alkyl, —OSO$_2$C$_{6-14}$aryl, —(CS)R$^7$, —O(CO)R$^7$, —(CO)R$^9$, a mono-, bi- or tricyclic saturated or mono- or polyunsaturated carbocycle with 3–14 ring members, mono-, bi- or tricyclic saturated or mono- or polyunsaturated heterocycle with 5–15 ring members and 1–6 heteroatoms, wherein the $C_{6-14}$ aryl groups and the included carbocylic and heterocyclic substituents can be optionally substituted one or more times by $R^{10}$, a mono- or polyunsaturated, straight-chain or branched-chain $C_{2-12}$alkenyl residue optionally substituted one or more times by —OH, —SH, —NH$_2$, —NHC$_{1-6}$alkyl, —N(CH$_{1-6}$ alkyl)$_2$, —NHC$_{6-14}$aryl, —N(C$_{6-14}$aryl)$_2$, —N(C$_{1-6}$alkyl)(C$_{6-14}$aryl), —NHCOR$^7$, —NO$_2$, —CN, —F, —Cl, —Br, —I, —O—C$_{1-6}$alkyl, —O—C$_{6-14}$-aryl, —O(CO)R$^7$, —S—C$_{1-6}$alkyl, —S—C$_{6-14}$aryl, —SOR$^8$, —SO$_2$R$^8$, —OSO$_2$C$_{1-6}$alkyl, —OSO$_2$C$_{6-14}$aryl, —(CS)R$^7$, —O(CO)R$^7$, —(CO)R$^9$, mono-, bi- or tricyclic saturated or mono- or polyunsaturated carbocycle with 3–14 ring members, a mono-, bi- or tricyclic saturated or mono- or polyunsaturated heterocycle with 5–15 ring members and 1–6 heteroatoms, the $C_{6-14}$ aryl groups and the included carbocyclic and heterocyclic substituents can be optionally substituted one or more times by $R^{10}$, mono-, bi- or tricyclic saturated or mono- or polyunsaturated carbocycle with 3–14 ring members, optionally substituted one or more times by —OH, —SH, —NH$_2$, —NH C$_{1-6}$alkyl, —N(C$_{1-6}$alkyl)$_2$, —NHC$_{6-14}$aryl, —N(C$_{6-14}$aryl)$_2$, —N(C$_{1-6}$alkyl)(C$_{6-14}$aryl), —NHCOR$^7$, —NO$_2$, —CN, —F, —Cl, —Br, —I, —O—C$_{1-6}$-alkyl, —O—C$_{6-14}$aryl, —O(CO)R$^7$, —S—C$_{1-6}$ alcyl, —S—C$_{6-14}$aryl, —SOR$^8$, —SO$_2$R$^8$, —OSO$_2$C$_{1-6}$alkyl, —OSO$_2$C$_{6-14}$aryl, —(CS)R$^7$, —O(CO)R$^7$, —(CO)R$^9$, the $C_{6-14}$ aryl groups can be optionally substituted one or more times by $R^{10}$, a mono-, bi- or tricyclic saturated or mono- or polyunsaturated heterocycle with 5–15 ring members and 1–6 heteroatoms, optionally substituted one or more times by —OH, —SH, —NH$_2$, —NHC$_{1-6}$alkyl, —N(C$_{1-6}$alkyl)$_2$, —NHC$_{6-14}$aryl, —N(C$_{6-14}$aryl)$_2$, —N(C$_{1-6}$alkyl)(C$_{6-14}$aryl), —NHCOR$^7$, —NO$_2$, —CN, —F, —Cl, —Br, —I, —O—C$_{1-6}$alkyl, —O—C$_{6-14}$aryl. —O(CO)R$^7$, —S—C$_{1-6}$alkyl, —S—C$_{6-14}$aryl, —SOR$^8$, —SO$_2$R$^8$, —OSO$_2$C$_{1-6}$alkyl, —OSOC$_2$C$_{6-14}$aryl, —(CS)R$^7$, —O(CO)R$^7$—(CO)R$^8$, the C$_{6-14}$aryl groups can be optionally substituted one or more times by $R^{10}$, carbo- or a heterocyclic saturated or mono- or polyunsaturated spirocycles with 3–10 ring members, where heterocyclic systems contain 1–6 heteroatoms optionally substituted one or more times by —OH, —SH, —NH$_2$, —NHC$_{1-6}$alkyl, —N(C$_{1-6}$alkyl)$_2$, —NHC$_{6-14}$aryl, —N(C$_{6-14}$aryl)$_2$, —N(C$_{1-6}$alkyl)(C$_{6-14}$aryl), —NHCOR$^7$, —NO$_2$, —CN, —F, —Cl, —Br, —I, —O—C$_{1-6}$ alkyl, —O—C$_{6-14}$aryl, —O(CO)R$^7$, —S—C$_{1-6}$alkyl, —S—C$_{6-14}$aryl, —SOR$^8$, —SO$_2$R$^8$, —OSO$_2$C$_{1-6}$alkyl, —OSO$_2$C$_{6-14}$ aryl, —(CS)R$^7$, —O(CO)R$^7$, —(CO)R$^8$, the C$_{6-4}$aryl groups can be optionally substituted one or more times by $R^{10}$;

$R^2$, $R^3$, $R^4$, $R^5$, $R^6$ can be the same or different and are hydrogen, and a straight-chaim or branched-chain C$_{1-6}$alkyl residue, optionally substituted one or more times by —OH, —SH, —NH$_2$, —NHC$_{1-6}$alkyl, —N(C$_{1-6}$alkyl)$_2$, —NHC$_{6-14}$aryl, —N(C$_{6-14}$aryl)$_2$, —N(C$_{1-6}$ alkyl)(C$_{6-14}$aryl), —NHCOR$^7$, —NO$_2$, —CN, —(CO)R$^8$, —(CS)R$^7$, —F, —Cl, —Br, —I, —O—C$_{1-6}$ akyl, —O—C$_{6-14}$aryl, —O(CO)R$^7$, —S—C$_{1-6}$alkyl, —S—C$_{6-14}$aryl, —SOR$^8$, —SO$_2$R$^8$, CO—C$_{1-6}$ alkyl, optionally substituted one or more times by —OH, —SH, —NH$_2$, —NHC$_{1-6}$alkyl, —N(C$_{1-6}$ alkyl)$_2$, —NHC$_{6-14}$aryl, —N(C$_{6-14}$aryl)$_2$, —N(C$_{1-6}$alkyl) (C$_{6-14}$aryl), —NHCOR$^7$, —NO$_2$, —CN, —(CO)R$^8$, —(CS)R$^7$, —F, —Cl, —Br, —I, —O—C$_{1-6}$alkyl, —O—C$_{6-14}$aryl, —O(CO)R$^7$, —S—C$_{1-6}$ alkyl, —S—C$_{6-14}$aryl, —SOR$^8$, —SO$_2$R$^8$ COO—C$_{1-6}$alkyl residue, optionally substituted one or more times by —OH, —SH, —NH$_2$, —NHC$_{1-6}$alkyl, —N(C$_{1-6}$ alkyl)$_2$, —NHC$_{6-14}$aryl, —N(C$_{6-14}$aryl)$_2$, —N(C$_{1-6}$alkyl)(C$_{6-14}$aryl), —NHCOR$^7$, —NO$_2$, —CN, —(CO)R$^8$, —(CS)R$^7$, —F, —Cl, —Br, —I, —O—C$_{1-6}$alkyl, —O—C$_{6-14}$aryl, —O(CO)R$^7$, —S—C$_{1-6}$alkyl, —S—C$_{6-14}$aryl, —SOR$^8$, —SO$_2$R$^8$;

$R^7$ is a C$_{1-6}$alkyl, —O—C$_{1-6}$alkyl, —O—C$_{6-14}$aryl, —NH$_2$, —NHC$_{1-6}$alkyl, —N(C$_{1-6}$alkyl)$_2$ —NHC$_{6-14}$aryl, —N(C$_{6-14}$aryl)$_2$, —N(C$_{1-6}$alkyl)(C$_{6-14}$aryl), —S—C$_{1-6}$alkyl, residue, or a mono-, bi- or tricyclic saturated or mono- or polyunsaturated carbocycle with 3–14 ring members, or mono-, bi- or tricyclic saturated or mono- or polyunsaturated heterocycle with 5–15 ring members and 1–6 heteroatoms, $R^8$ is —H, a —C$_{1-6}$alkyl, —NH$_2$, —NHC$_{1-6}$alkyl, —N(C$_{1-6}$alkyl)$_2$, —NHC$_{6-14}$aryl, —N(C$_{6-14}$aryl)$_2$, —N(C$_{1-6}$alkyl)(C$_{6-14}$aryl), —NHCOR$^7$, —OH, —O—C$_{1-6}$alkyl, —O—C$_{6-14}$aryl), —S—C$_{1-6}$alkyl, —S—C$_{6-14}$aryl residue, or a mono-, bi- or tricyclic saturated or mono- or polyunsaturated carbocycle with 3–14 ring members, or mono-, bi- or tricyclic saturated or mono- or polyunsaturated heterocycle with 5–15 ring members and 1–6 hetero atoms;

$R^9$ is —H, a —C$_{1-6}$alkyl residue, or mono-, bi- or tricyclic saturated or mono- or polyunsaturated carbocycle with 3–14 ring members, or a mono-, bi- or tricyclic saturated or mono- or polyunsaturated heterocycle with 5–15 ring members and 1–6 heteroatoms, $R^{10}$ is —OH, a —SH, —NH$_2$, —NHC$_{1-6}$alkyl, —N(C$_{1-6}$akyl)$_2$, —NHC$_{6-14}$aryl, —N(C$_{6-14}$aryl)$_2$, —N(C$_{1-6}$alkyl)(C$_{6-14}$aryl), —NHCOR$^7$, —NO$_2$, —CN, —(CO)R$^8$, —(CS)R$^7$, —F, —Cl, —Br, —I, —O—C$_{1-6}$alkyl, —O—C$_{6-14}$aryl, —O(CO)R$^7$, —S—C$_{1-6}$alkyl, —S—C$_{6-14}$aryl, —SOR$^8$, or an —SO$_2$R$^8$ residue, and A, B can be a —CH$_2$—, —CH(OH) residue or A+B can be a —CH=CH— residue, or with a pharmaceutically acceptable salt thereof, provided that $R^2$ through $R^5$ are not hydrogen when $R^6$ is CH$_3$.

2. Pharmaceutically acceptable salts of the compounds of claim 1, obtained by neutralization of the bases with inorganic or organic acids or by neutralization of the acids with inorganic or organic acids or by neutralization of the acids with inorganic or organic bases or by quaternization of tertiary amines to provide quaternary ammonium salts.

3. The compounds:

2-phenyl-10,12,15,16-tetrahydroxy-8-methoxy-11-methyl-9,14-dioxo-6,7,9,14-tetrahydronaphthaceno[1,2-g]phthalazin-1-one;

10,12,15,16-tetrahydroxy-8-methoxy-11-methyl-9,14-dioxo-6,7,9,14-tetrahydronaphthaceno[1,2-g]phthalazin-1-one;

2-methyl-10,12,15,16-tetrahydroxy-8-methoxy-11-methyl-9,14-dioxo-6,7,9,14-tetrahydronaphthaceno[1,2-g]phthalazin-1-one;

2-propyl-10,12,15,16-tetrahydroxy-8-methoxy-11-methyl-9,14-dioxo-6,7,9,14-tetrahydronaphthaceno[1,2-g]phthalazin-1-one;

2-(2-hydroxyethyl)-10,12,15,16-tetrahydroxy-8-methoxy-11-methyl-9,14-dioxo-6,7,9,14-tetrahydronaphthaceno[1,2-g]phthalazin-1-one;

2-(2-acetoxyethyl)-10,12,15,16-tetrahydroxy-8-methoxy-11-methyl-9,14-dioxo-6,7,9,14-tetrahydronaphthaceno[1,2-g]phthalazin-1-one;

2-(2-aminoethyl)-10,12,15,16-tetrahydroxy-8-methoxy-11-methyl-9,14-dioxo-6,7,9,14-tetrahydronaphthaceno[1,2-g]phthalazin-1-one;

2-(2,2-diethoxyethyl)-10,12,15,16-tetrahydroxy-8-methoxy-11-methyl-9,14-dioxo-6,7,9,14-tetrahydronaphthaceno[1,2-g]phthalazin-1-one;

2-(2-imidazolyl)-10,12,15,16-tetrahydroxy-8-methoxy-11-methyl-9,14-dioxo-6,7,9,14-tetrahydronaphthaceno[1,2-g]phthalazin-1-one;

2-(2-pyridyl)-10,12,15,16-tetrahydroxy-8-methoxy-11-methyl-9,14-dioxo-6,7,9,14-tetrahydronaphthaceno[1,2-g]phthalazin-1-one;

2-2-pyridyl)-8,10,12,15,16-pentahydroxy-11-methyl-9,14-dioxo-6,7,9,14-tetrahydronaphthaceno[1,2-g]phthalazin-1-one;

2-phenyl-8,10,12,15,16-pentahydroxy-11-methyl-9,14-dioxo-6,7,9,14-tetrahydronaphthaceno[1,2-g]phthalazin-1-one;
  2-phenyl-10,15,16-trihydroxy-8-methoxy-12-methoxycarbonyloxy-11-methyl-9,14-dioxo-6,7,9,14-tetrahydronaphthaceno[1,2-g]phthalazin-1-one;

2-phenyl-10,12,15,16-tetraacetoxy-8-methoxy-11-methyl-9,14-dioxo-6,7,9,14-tetrahydronaphthaceno[1,2-g]phthalazin-1-one;

2-phenyl-12-allyl-10,15,16-trihydroxy-8-methoxy-11-methyl-9,14-dioxo-6,7,9,14-tetrahydronaphthaceno[1,2-g]phthalazin-1-one;

2-phenyl-10,12,15,16-tetrahydroxy-8-methoxy-11-methyl-9,14-dioxo-9,14-dihydronaphthaceno[1,2-g]phthalazin-1-one; and 2-phenyl-6,7,10,12,15,16-hexahydroxy-8-methoxy-11-methyl-9,14-dioxo-6,7,9,14-tetrahydronaphthaceno[1,2-g]phthalazin-1-one.

4. A composition which comprises a compound or salt of claim 1, further comprising a pharmaceutically acceptable carrier and/or diluent or excipient.

5. A process for preparing the composition of claim 4, which comprises admixing a compound or salt of claim 1, with a pharmaceutical carrier and/or diluent or other excipient to obtain a pharmaceutical preparation, or are bringing the drug into a dosage form that is useful for administration.

6. A process for inhibiting the action of the cytokines interleukin-2, interleukin-4, and interleukin-5, which comprises administering to a patient in need therefore a compound of Formula 4

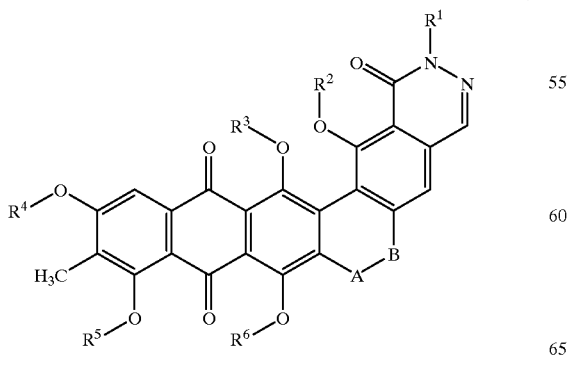

4 wherein
  $R^1$ is hydrogen, or branched-chain, or straight-chain $C_{1-12}$alkyl residue optionally substituted one or more times by —OH, —SH, —NH$_2$, —NHC$_{1-6}$alkyl, —N(C$_{1-6}$alkyl)$_2$, —NHC$_{6-14}$alkyl, —N(C$_{6-14}$alkyl)$_2$, —N(C$_{1-6}$alkyl)(C$_{6-14}$aryl), —NHCOR$^7$, —NO$_2$, —CN, —F, —Cl, —Br, —I, —O—C$_{1-6}$alkyl, —O—C$_{6-14}$aryl, —O(CO)R$^7$, —S—C$_{1-6}$-alkyl, —S—C$_{6-14}$aryl, —SOR$^8$, —SO$_2$R$^8$, —OSO$_2$C$_{1-6}$alkyl, —OSO$_2$C$_{6-14}$aryl, —(CS)R$^7$, —O(CO)R$^7$, —(CO)R$^9$, a mono-, bi- or tricyclic saturated or mono- or polyunsaturated carbocycle with 3–14 ring members, mono-, bi- or tricyclic saturated or mono- or polyunsaturated heterocycle with 5–15 ring members and 1–6 heteroatoms, wherein the C$_{6-14}$ aryl groups and the included carbocyclic and heterocyclic substituents can be optionally substituted one or more times by $R^{10}$, a mono- or polyunsaturated, straight-chain or branched-chain C$_{2-12}$alkenyl residue optionally substituted one or more times by —OH, —SH, —NH$_2$, —NHC$_{1-6}$akyl, —N(C$_{1-6}$ alkyl)$_2$, —NHC$_{6-14}$aryl, —N(C$_{6-14}$aryl)$_2$, —N(C$_{1-6}$alkyl)(C$_{6-14}$aryl), —NHCOR$^7$, —NO$_2$, —CN, —F, —Cl, —Br, —I, —O—C$_{1-6}$alkyl, —O—C$_{6-14}$-aryl, —O(CO)R$^7$, —S—C$_{1-6}$alkyl, —S—C$_{6-14}$-aryl, —SOR$^8$, —SO$_2$R$^8$, —OSO$_2$C$_{1-6}$alkyl, —OSO$_2$C$_{6-4}$aryl, —(CS)R$^7$, —O(CO)R$^7$, —(CO)R$^9$, mono-, bi- or tricyclic saturated or mono- or polyunsaturated carbocycle with 3–14 ring members, a mono-, bi- or tricyclic saturated or mono- or polyunsaturated heterocycle with 5–15 ring members and 1–6 heteroatoms, the C$_{6-14}$ aryl groups and the included carbocyclic and heterocyclic substituents can be optionally substituted one or more times by $R^{10}$, mono-, bi- or tricyclic saturated or mono- or polyunsaturated carbocycle with 3–14 ring members, optionally substituted one or more times by —OH, —SH, —NH$_2$, —NH C$_{1-6}$ alkyl, —N(C$_{1-6}$alkyl)$_2$, —NHC$_{6-14}$aryl, —N(C$_{6-14}$aryl)$_2$, —N(C$_{1-6}$alkyl)(C$_{6-14}$aryl), —NHCOR$^7$, —NO$_2$, —CN, —F, —Cl, —Br, —I, —O—C$_{1-6}$-alkyl, —O—C$_{6-4}$aryl, —O(CO)R$^7$, —S—C$_{1-6}$alkyl, —S—C$_{6-14}$aryl, —SOR$^8$, —SO$_2$R$^8$, —OSO$_2$C$_{1-6}$alkyl, —OSO$_2$C$_{6-14}$aryl, —(CS)R$^7$, —O(CO)R$^7$, —(CO)R$^9$, the C$_{6-14}$ aryl groups can be optionally substituted one or more times by $R^{10}$, a mono-, bi- or tricyclic saturated or mono- or polyunsaturated heterocycle with 5–15 ring members and 1–6 heteroatoms, optionally substituted one or more times by —OH, —SH, —NH$_2$, —NHC$_{1-6}$alkyl, —N(C$_{1-6}$alkyl)$_2$, —NHC$_{6-14}$aryl, —N(C$_{6-14}$aryl)$_2$, —N(C$_{1-6}$ alkyl)(C$_{6-14}$aryl), —NHCOR$^7$, —NO$_2$, —CN, —F, —Cl, —Br, —I, —O—C$_{1-6}$alkyl, —O—C$_{6-14}$aryl, —O(CO)R$^7$, —S—C$_{1-6}$alkyl, —S—C$_{6-14}$aryl, —SOR$^8$, —SO$_2$R$^8$, —OSO$_2$C$_{1-6}$alkyl, —OSOC$_2$C$_{6-14}$ aryl, —(CS)R$^7$, —O(CO)R$^7$, —(CO)R$^8$, the C$_{6-14}$aryl groups can be optionally substituted one or more times by $R^{10}$, carbo- or a heterocyclic saturated or mono- or polyunsaturated spirocycles with 3–10 ring members, where heterocyclic systems contain 1–6 heteroatoms optionally substituted one or more times by —OH, —SH, —NH$_2$, —NHC$_{1-6}$alkyl, —N(C$_{1-6}$alkyl)$_2$, —NHC$_{6-14}$aryl, —N(C$_{6-14}$aryl)$_2$, —N(C$_{1-6}$alkyl)(C$_{6-14}$aryl), —NHCOR$^7$, —NO$_2$, —CN, —F, —Cl, —Br, —I, —O—C$_{1-6}$alkyl, —O—C$_{6-14}$aryl, —O(CO)R$^7$, —S—$C_{1-6}$alkyl, —S—$C_{6-14}$aryl, —$SOR^8$, —$SO_2R^8$, —$OSO_2C_{1-6}$ arkyl, —$OSO_2C_{6-14}$ aryl, —(CS)$R^7$, —O(CO)$R^7$, —(CO)$R^8$, the $C_{6-14}$aryl groups can be optionally substituted one or more times by $R^{10}$;

$R^2$, $R^3$, $R^4$, $R^5$, $R^6$ can be the same or different and are hydrogen, and a straight-chain or branched-chain $C_{1-6}$alkyl residue, optionally substituted one or more times by —OH, —SH, —$NH_2$, —$NHC_{1-6}$alkyl, —N($C_{6-14}$alkyl)$_2$, —$NHC_{6-14}$aryl, —N($C_{6-14}$aryl)$_2$, —N($C_{1-6}$ alkyl)($C_{6-14}$aryl), —$NHCOR^7$, —$NO_2$, —CN, —(CO)$R^8$, —(CS)$R^7$, —F, —Cl, —Br, —I, —O—$C_{1-6}$ alkyl, —O—$C_{6\ 14}$aryl, —O(CO)$R^7$, —S—$C_{1-6}$alkyl, —S—$C_{6-14}$aryl, —$SOR^8$, —$SO_2R^8$, CO—$C_{1-6}$ alkyl, optionally substituted one or more times by —OH, —SH, —$NH_2$, —$NHC_{1-6}$alkyl, —N($C_{1-6}$ alkyl)$_2$, —$NHC_{6-14}$aryl, —N($C_{6-14}$aryl)$_2$, —N($C_{1-6}$alkyl)($C_{6-14}$aryl), —$NHCOR^7$, —$NO_2$, —CN, —(CO)$R^8$, —(CS)$R^7$, —F, —Cl, —Br, —I, —O—$C_{1-6}$alkyl, —O—$C_{6-14}$aryl, —O(CO)$R^7$, —S—$C_{1-6}$ alkyl, —S—$C_{6-14}$aryl, —$SOR^8$, —$SO_2R^8$ COO—$C_{1-6}$alkyl residue, optionally substituted one or more times by —OH, —SH, —$NH_2$, —$NHC_{1-6}$alkyl, —N($C_{1-6}$alkyl)$_2$, —$NHC_{6-14}$aryl, —N($C_{6-14}$aryl)$_2$, —N($C_{1-6}$alkyl)($C_{6-14}$ aryl), —$NHCOR^7$, —$NO_2$, —CN, —(CO)$R^8$, —(CS)$R^7$, —F, —Cl, —Br, —I, —O—$C_{1-6}$alkyl, —O—$C_{6-14}$aryl, —O(CO)$R^7$, —S—$C_{1-6}$alkyl, —S—$C_{6-14}$aryl, —$SOR^8$, —$SO_2R^8$;

$R^7$ is a $C_{1-6}$alkyl, —O—$C_{1-6}$alkyl, —O—$C_{6-14}$aryl, —$NH_2$, —$NHC_{1-6}$alkyl, —N($C_{1-6}$alkyl)$_2$, —$NHC_{6-14}$aryl, —N($C_{6-14}$aryl)$_2$, —N($C_{1-6}$alkyl)($C_{6-14}$aryl), —S—$C_{1-6}$alkyl, —S—$C_{6-14}$aryl residue, or a mono-, bi- or tricyclic saturated or mono- or polyunsaturated carbocycle with 3–14 ring members, or mono-, bi- or tricyclic saturated or mono- or polyunsaturated heterocycle with 5–15 ring members and 1–6 heteroatoms, $R^8$ is —H, a —$C_{1-6}$alkyl, —$NH_2$, —$NHC_{1-6}$alkyl, —N($C_{1-6}$alkyl)$_2$, —$NHC_{6-14}$aryl, —N($C_{6-14}$aryl)$_2$, —N($C_{1-6}$alkyl)($C_{6-14}$aryl), —$NHCOR^7$, —OH, —O—$C_{1-6}$alkyl, —O—$C_{6-14}$aryl), —S—$C_{1-6}$alkyl, —S—$C_{6-14}$aryl residue, or a mono-, bi- or tricyclic saturated or mono- or polyunsaturated carbocycle with 3–14 ring members, or mono-, bi- or tricyclic saturated or mono- or polyunsaturated heterocycle with 5–15 ring members and 1–6 hetero atoms;

$R^9$ is —H, a —$C_{1-6}$alkyl residue, or mono-, bi- or tricyclic saturated or mono- or polyunsaturated carbocycle with 3–14 ring members, or a mono-, bi- or tricyclic saturated or mono- or polyunsaturated heterocycle with 5–15 ring members and 1–6 heteroatoms, $R^{10}$ is —OH, a —SH, —$NH_2$, —$NHC_{1-6}$alkyl, —N($C_{1-6}$alkyl)$_2$, —$NHC_{6-14}$aryl, —N($C_{6-14}$aryl)$_2$, —N($C_{1-6}$alkyl)($C_{6-14}$aryl), —$NHCOR^7$, —$NO_2$, —CN, —(CO)$R^8$, —(CS)$R^7$, —F, —Cl, —Br, —I, —O—$C_{1-6}$ alkyl, —O—$C_{6-14}$aryl, —O(CO)$R^7$, —S—$C_{1-6}$alkyl, —S —$C_{6-14}$aryl, —$SOR^8$, or an —$SO_2R^8$ residue, and A, B can be a —$CH_2$—, —CH(OH) residue or A+B can be a —CH═CH— residue, or with a pharmaceutically acceptable salt thereof.

7. The process of claim 6, wherein said heteroatom is N, O, or S.

* * * * *